(12) United States Patent
Li (10) Patent No.: US 9,770,547 B2
(45) Date of Patent: Sep. 26, 2017

(54) HEAT BALANCE TYPE CIRCULATING PIPE SYSTEM (71) Applicant: Wei Li, Shaanxi (CN)

(72) Inventor: Wei Li, Shaanxi (CN)

( * ) Notice: Subject to any disclaimer, the term of this patent is extended or adjusted under 35 U.S.C. 154(b) by 0 days.

(21) Appl. No.: 15/118,098

(22) PCT Filed: Jan. 14, 2016

(86) PCT No.: PCT/CN2016/070863
§ 371 (c)(1),
(2) Date: Aug. 11, 2016

(87) PCT Pub. No.: WO2016/145941
PCT Pub. Date: Sep. 22, 2016

(65) Prior Publication Data
US 2017/0165409 A1 Jun. 15, 2017

(30) Foreign Application Priority Data
Mar. 13, 2015 (CN) .......................... 2015 1 0111569

(51) Int. Cl.
*A61M 1/36* (2006.01)
*A61F 7/00* (2006.01)
(Continued)

(52) U.S. Cl.
CPC ............ *A61M 1/369* (2013.01); *A61F 7/0085* (2013.01); *A61M 1/0025* (2014.02); *A61M 1/10* (2013.01);
(Continued)

(58) Field of Classification Search
CPC ...... A61M 1/00; A61M 1/0058; A61M 1/369; A61M 5/44; A61M 2205/128;
(Continued)

(56) References Cited

U.S. PATENT DOCUMENTS 4,476,867 A * 10/1984 Parks .................. A61M 1/3655
165/253
6,610,024 B1 * 8/2003 Benatti ............... A61M 1/3621
604/19

(Continued)

FOREIGN PATENT DOCUMENTS

CN 201798953 U 4/2011

*Primary Examiner* — Quynh-Nhu H Vu
(74) *Attorney, Agent, or Firm* — Gokalp Bayramoglu (57) ABSTRACT A heat-balance-type circulating pipe system, comprising a control system connected with a circulating hyperthermal perfusion heating device and a perfusion device; the circulating hyperthermal perfusion heating device comprises molecular rings, a plurality of magnetic field generators for heating a heating tank, an induction ring and a heater consisting of inductors; the inlet and the outlet connecting member of the perfusion device are communicated and then connected to the infusion member through a three-way joint; the inlet and the outlet connecting member are respectively connected with the heating tank; the heating tank comprises an outer and an inner tank; the inner heating tank is internally provided with an inner stirrer and an upper heating tank covered with a temperature control and detection sensor. The heat exchange efficiency is high; the hyperthermic perfusion therapeutic effect is good; and quick and uniform heat effect is good.

10 Claims, 5 Drawing Sheets (51) Int. Cl.
*A61M 1/10* (2006.01)
*A61M 1/34* (2006.01)
*A61M 1/00* (2006.01)

(52) U.S. Cl.
CPC .......... *A61M 1/342* (2013.01); *A61M 1/3621* (2013.01); *A61M 2205/3368* (2013.01); *A61M 2205/3653* (2013.01)

(58) Field of Classification Search
CPC ........ A61M 2205/36; A61M 2205/366; A61M 2210/1017; A61M 31/00; A61M 1/0025; A61M 1/10; A61M 1/342; A61M 1/3621; A61M 2205/3368; A61M 2205/3653; A61F 7/00; A61F 7/12; A61F 7/0085; A61F 2007/126; A61F 2007/0018; A61F 2007/0069
See application file for complete search history.

(56) References Cited

U.S. PATENT DOCUMENTS

| | | | | |
|---|---|---|---|---|
| 2009/0043256 | A1* | 2/2009 | Landy | A61M 5/1407 604/113 |
| 2010/0298771 | A1* | 11/2010 | Tan | A61M 5/44 604/113 |
| 2014/0031631 | A1* | 1/2014 | Hall | A61F 7/12 600/205 |

* cited by examiner

HEAT BALANCE TYPE CIRCULATING PIPE SYSTEM

BACKGROUND OF THE INVENTION

The present invention relates to a medical device, in particular to a heat-balance-type circulating pipe system.

Cancers in the pleuroperitoneal cavity tend to transfer and relapse, causing a lot of cancer-related effusion in the cavity. In particular, 50% of patients with gastrointestinal cancer suffer the same disease usually within one year after the operation, 80% within two years, and up to 90% within four years, which is the major fatal cause.

At present, the chemotherapy of cancers in the pleuroperitoneal cavity and the ascites concentration and reinfusion therapy are carried out using a hyperthermia perfusion instrument. The hyperthermia perfusion instrument mainly includes a control system, a heating device and a perfusion system; the heating device and the perfusion system are both connected with the control system and controlled by the control system.

However, the circulating pipes of the existing perfusion system is single-layer, so the temperature preservation effect is poor, and the heat loss is large. The heating system is an electromagnetic induction heating structure. Electromagnetic induction heating can generate heat quickly, but only a single face or point is heated, so a part of the liquid in the perfusion tank is heated while the other is not, which easily causes non-uniform heating. At the same time, the infusion member in the perfusion system is exposed outside, the liquid easily cools down, and so the temperature preservation effect is inadequate. Therefore, a heating device is needed to heat repeatedly, causing large power loss.

Meanwhile, existing perfusion systems can only simply store the liquid with cancer cells in the perfusion tank and cannot handle the liquid effectively, and the heating system heats the liquid in the perfusion tank at a single point so that the liquid temperature in the perfusion tank is not uniform.

Existing heating systems can only maintain the desired temperature after heating the liquid in the perfusion tank, so when the liquid entering the abdominal cavity is hot, the existing heating system cannot cool the hot liquid and can only perform simple single perfusion into the pipe. Meanwhile, the temperature of the liquid in the infusion member also quickly reduces along with the air flow.

BRIEF SUMMARY OF THE INVENTION

Aiming at defects in the prior art, the objective of the present invention is to provide a heat-balance-type circulating pipe system to solve various problems in the prior art.

The objective of the present invention can be fulfilled by the following technical solution:

A heat balance type circulating pipe system includes a control system, a circulating hyperthermal perfusion heating device and a perfusion device; the circulating hyperthermal perfusion heating device and a perfusion device are both connected with the control system, and controlled by the control system; the circulating hyperthermal perfusion heating device includes molecular rings and a heater for heating the heating tank; the heater includes a base and a sleeve installed on the base; the sleeve is wound with an induction coil; the sleeve wound with the induction coil is coaxially sleeved with a plurality of magnetic field generators for performing induction heating on the heating tank; the magnetic field generators are externally sleeved with molecular rings; the sleeve is provided an internal heating tank, which is placed in the perfusion device;

The perfusion device includes an inlet connecting member in connection with a body cavity, an outlet connecting member in connection with the body cavity, an infusion member and the heating tank; the inlet connecting member is communicated with the outlet connecting member, while the inlet connecting member and the outlet connecting member are both connected with the infusion member through a tee joint; the inlet connecting member and the outlet connecting member are respectively connected with the heating tank through a connecting pipe; the body cavity, the inlet connecting member, the heating tank and the outlet connecting member are connected in turn to form a system of external circulation; an inlet and an outlet of the heating tank are connected through a right circulating pipe to form a closed loop which is of internal circulation; the heating tank includes an outer heating tank and an inner heating tank which are sleeved together; a closed cavity with an inlet and an outlet is formed between the inner heating tank and the outer heating tank; the inner heating tank is internally and horizontally provided with an inner stirrer; the inner heating tank is provided with an upper heating tank cover which has inlet and outlet pipes and a temperature control and detection sensor implanting entrance; and the temperature control and detection sensor implanting entrance is internally provided with a temperature control and detection sensor and a sensor rubber plug.

The outlet connecting member includes an outlet connector, an outlet temperature sensor disposed on the outlet connector, an outlet connecting pipe and an outlet pipe clamp disposed on the outlet connecting pipe; one end of the outlet connecting pipe is connected with the outlet connector, while the other end is connected with a port through a first tee joint; the outlet connecting pipe at the front end of the outlet pipe clamp is also connected with a molecular filter for filtering cells in liquid in the body cavity during filtrating and circulation; the inlet connecting member includes an inlet connector, an inlet temperature sensor disposed on the inlet connector; an inlet connecting pipe and an inlet pipe clamp disposed on the inlet connecting pipe; one end of the inlet connecting pipe is connected with the inlet connector, while the other end is connected with one outlet of a temperature buffering device; another outlet of the temperature buffering device is connected with a port of the first tee joint through a connecting pipe; an inlet of the temperature buffering device is communicated with a heating tank; the temperature buffering device is also formed with a temperature detection opening and a sampling opening; the inlet connector is also connected with a drainage tube with a drainage tube clamp; the end of the drainage tube is provided with a drainage tube transition joint for being connected with a drained liquid bottle; and the outlet connector is connected with a drain system.

The drain system includes a liquid discharge pipe; the liquid discharge pipe is connected to the outlet connector; the liquid discharge pipe is connected with a body pipe clamp, a flow meter, a plurality of peristaltic pumps and an outlet pipe clamp in turn; the liquid discharge pipe at one end of the body pipe clamp is shunted into two paths, one connected with a body liquid collector and the other directly connected with the connecting pipe.

The perfusion device also includes a perfused power pump for providing driving force for the circulation of the perfused liquid; the perfused power pump is disposed between the connecting pipe between the heating tank and the outlet connecting member; the inlet connecting pipe of the inlet connecting member is provided with a drug-feeding opening for injecting drugs and a flow meter for measuring the flow; the inlet connector is also connected with a movable inlet connecting pipe; the heating tank is also provided with an air exhaust pipe for exhausting air in the heating tank; and the air exhaust pipe is provided with an air exhaust pipe clamp.

The pipes in the inlet connecting member are pipes with dual-layer walls, and the space between the inner and outer layers of the walls is in vacuum.

The bottom of the base of the heater is also provided with a mixing device for uniformly mixing the liquid in the heating tank which is placed in the heater.

The closed cavity formed between the inner heating tank and the outer heating tank is filled with radiative substances which kill cancer cells.

The infusion member is internally provided with a thermostatic chamber; the liquid outlet end of the infusion member is provided with a physical filter for filtering impurities in the initially perfused liquid.

The temperature buffering device is a temperature buffering tank; the temperature buffering tank includes an outer temperature buffering tank and an inner temperature buffering tank which are sleeved together; the inner temperature buffering tank and the outer temperature buffering tank form vacuum there-between; the internal temperature buffering tank is internally and horizontally provided with an inner stirrer; the internal temperature buffering tank is provided with an upper temperature buffering tank cover; the upper temperature buffering tank cover is provided with two outlets, one inlet, a temperature detection opening and a sampling opening; the temperature buffering tank is also provided with an air exhaust pipe for exhausting air in the heating tank; and the air exhaust pipe is provided with an air exhaust pipe clamp.

Each magnetic field generator includes an upper annular fixed rings and a lower annular fixed rings; a plurality of columnar magnetic bars are installed between the upper and lower two annular fixed rings at an interval; and the inner stirrer is an impeller.

Compared with the prior art, the present invention has the following beneficial effects:

Through configuration of the molecular rings and the heater consisting of a plurality of magnetic field generators, the induction coil wound on the sleeve and the inductor disposed in the heating tank, the heat-balance-type circulating pipe system provided by the present invention changes the original heating mode in which the heating tank is heated according to the water temperature into a layered, alternative, multi-frequency and multi-point heating mode by adjusting one or more magnetic generators, so the heating is uniform; the problem of the heating not being uniform, as caused by heating one surface or at one point, is overcome; and uniform and quick water heating is achieved. Meanwhile, in the present invention, a molecular ring, an auxiliary heating device, is used to heat and handle the heating tank. The molecular ring is a closed energy ring, which stores a substance's molecular vibration waves in the liquid in a heating tank on the basis of quantum physics, and can steadily release the energy at a constant quantity. The liquid accepts the vibration waves and transmits the vibration waves toward the flowing direction of the liquid, and the activities of the liquid is greatly intensified by the effect of the vibration waves. The effect is to improve the properties of the circulating liquid, improve heat exchange efficiency, decompose the bacterial residue, and avoid the generation of drug resistance. By the auxiliary effect of the molecular ring, the cancer cells in the heating tank can be decomposed, thus fulfilling the aim of effective handling of the cancer cells.

Meanwhile, the heating tank is internally provided with an inner stirrer, so liquid entering the heating tank automatically flows to impact the inner stirrer and drive the inner stirrer to rotate, thus fulfilling the aims of stirring the liquid, making the water temperature in the heating tank uniform, avoiding large differences in water temperature in the upper and lower layers due to non-uniform heating and effectively preventing occurrence of excessive water temperature shock. Therefore, by the effect of the inner stirrer and the heater, the heat-balance-type circulating pipe system can achieve good perfusion.

Meanwhile, the heating tank is a dual-layer structure and can be added with radiative substances. The radiative substances can irradiate and kill cancer cells and effectively handle the cancer cells, thus improving the therapeutic effect and releasing pains on the patients.

Further, the wall of the pipe in the inlet connecting member is a dual-layer pipe wall, and the space between the inner and outer pipe walls is in vacuum, thus realizing temperature preservation and control. The vacuum layer completely eradicates heat conduction and heat convection with the existence of the air layer, reduces the conduction and heat loss, greatly mitigates heat loss and achieves a good heat preservation effect. Compared with the structure of the air layer, a temperature loss of 5-8° can be prevented.

Further, with the configuration of the drain system, the present invention enlarges the application scope of the perfusion machine and improves the function of the instrument in comparison with single-mode perfusion.

Further, the bottom of the heater is provided with a mixing device, so the liquid entering the heating tank can be uniformly mixed, thus improving the therapeutic effect.

Further, one end of the outlet connecting member close to the outlet pipe clamp is also connected with a molecular filter. In this way, the residual cells left after radiotherapy can be filtered to remove cancer cells and substances stimulating the cancer to grow, which flow back to the liquid in the heating tank.

The infusion member is internally provided with a thermostatic chamber to keep the temperature of the liquid in the infusion member consistent with the temperature of the environment where the machine is used such that the temperature difference is not too large.

Further, the present invention is added with a temperature buffering device. When the heated liquid flows into the device, secondary mixing can be performed quickly to prevent occurrence of excessive temperature shock. When the inlet path is blocked, the temperature of the whole heating tank can be still kept constant in the circulation, thus playing the role of stabilizing the temperature.

The present invention has a simple structure and is low in cost.

Wherein, 1 outlet connector; 2 outlet temperature sensor implanting entrance; 3 outlet pipe clamp; 4 inlet connector; 5 inlet temperature sensor implanting entrance; 6 drainage tube clamp; 7 inlet pipe clamp; 8 drainage tube transition joint; 9 drug-feeding opening; 10 flow meter; 11 heating tank; 12 temperature control and detection sensor implanting entrance; 13 air exhaust pipe clamp; 14 air exhaust pipe; 15 perfused power pump, 16 infusion pipe clamp; 17 bottle needle; 18 outlet connecting pipe; 19 temperature buffering device; 191 temperature detection opening; 192 sampling opening; 20 first tee joint; 21 inlet connecting pipe; 22 drainage tube; 23 first connecting pipe; 24 second connecting pipe; 25 molecular ring; 26 heater; 261 base; 262 heating ring; 263 sleeve; 264 upper annular fixed ring; 265 columnar magnetic bar; 266 lower annular fixed ring; 111 outer heating tank; 112 inner heating tank; 113 inner stirrer; 114 upper heating tank cover; 115 sensor rubber plug; 27 molecular filter; 28 physical filter; 29 liquid discharge pipe; 30 body pipe clamp I; 31 flow meter; 32 peristaltic pump; 33 body pipe clamp II; 34 body liquid collector; 35-(1-4) control system valve; 361 inner layer of dual-layer wall; 362 outer layer of dual-layer wall; 37 drained liquid bottle.

DETAILED DESCRIPTION OF THE INVENTION

The present invention is described in further detail with reference to the specific embodiments, which is not limited to, but is an explanation of, the present invention.

Refer to FIG. 1-8. A heat-balance-type circulating pipe system includes a control system, a circulating hyperthermal perfusion heating device and a perfusion device. The circulating hyperthermal perfusion heating device and a perfusion device are both connected with the control system, and controlled by the control system; the circulating hyperthermal perfusion heating device includes molecular rings 25 and a heater 26 for heating the heating tank 11; the heater 26 includes a base 261 and a sleeve 263 installed on the base; the sleeve 263 is wound with an induction coil; the sleeve 263 wound with the induction coil is coaxially sleeved with a plurality of magnetic field generators 262 for performing induction heating on the heating tank 11; the magnetic field generators 262 are externally sleeved with molecular rings 25; the sleeve 263 is provided an internal heating tank 11, which is placed in the perfusion device to prevent the heating device from generating excessive temperature shock thereon during heating; the heating tank 11 is internally provided with induction magnetic field generators and an inductor for inducing the magnetic field generated by the coil; when the heating tank is heated, the heat generated during the mutual induction among the three magnetic field generators, the induction coil wound on the sleeve 263 and the inductor placed in the heating tank, can be used respectively to heat the heating tank 11, or heat the heating tank by layer, or heat the heating tank alternatively, or heat the heating tank at the same time, or heat the heating tank by multiple frequency at multiple points, so the heating is uniform, the heating efficiency is improved, and the probability of damage to the ingredients of the heated liquid is minimized. Wherein, each magnetic field generator 262 includes an upper annular fixed rings 264 and a lower annular fixed rings 266, and a plurality of columnar magnetic bars 265 are installed between the upper and lower two annular fixed rings at an interval.

Figure 4:
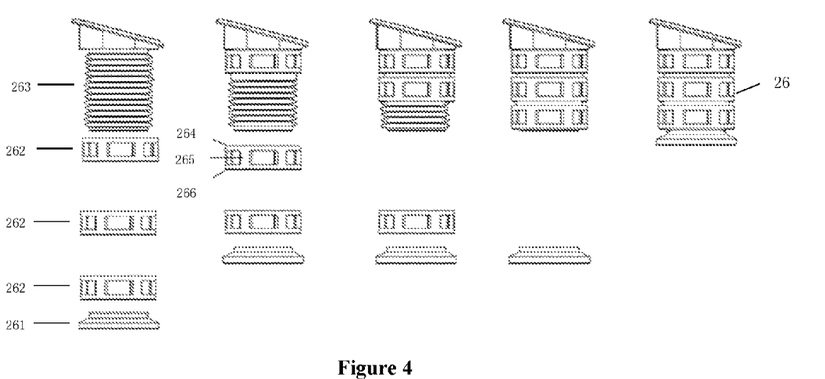
FIG. 4 is a structural view of the heater provided by the present invention.

The bottom of the base 261 of the heater 26 is also provided with a mixing device for uniformly mixing the liquid in the heating tank which is placed in the heater. In this way, the cancer-cell-killing performance of the therapeutic effect of the heating tank is further improved.

Figure 1:
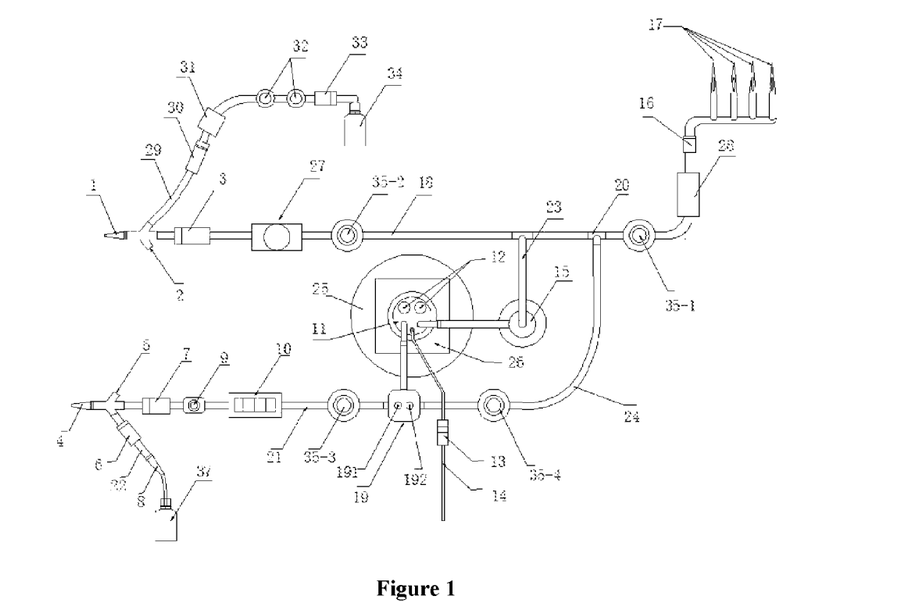
FIG. 1 is an overall structural view of the heat-balance-type circulating pipe system provided by the present invention.
Figure 2:
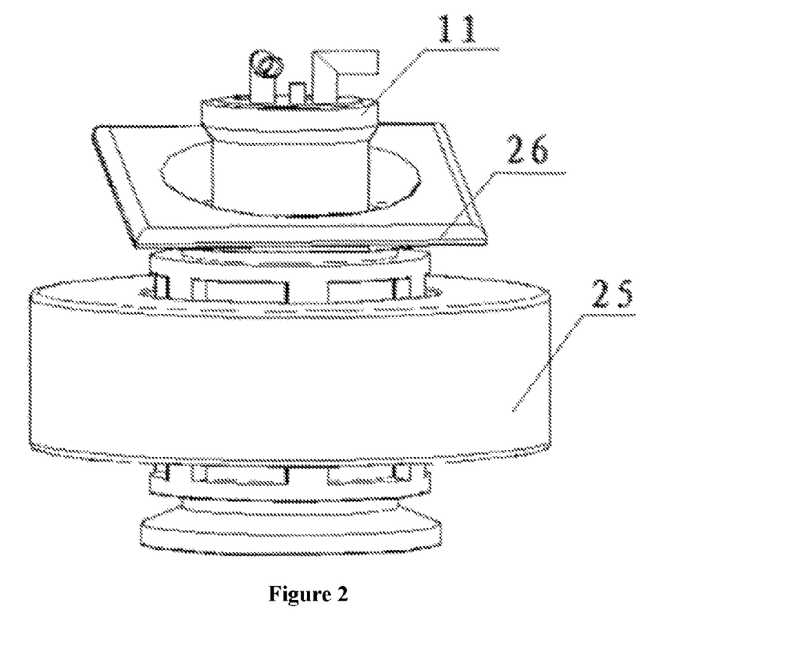
FIG. 2 is a structural view 1 of the circulating hyperthermic perfusion and heating device provided by the present invention.
Figure 3:
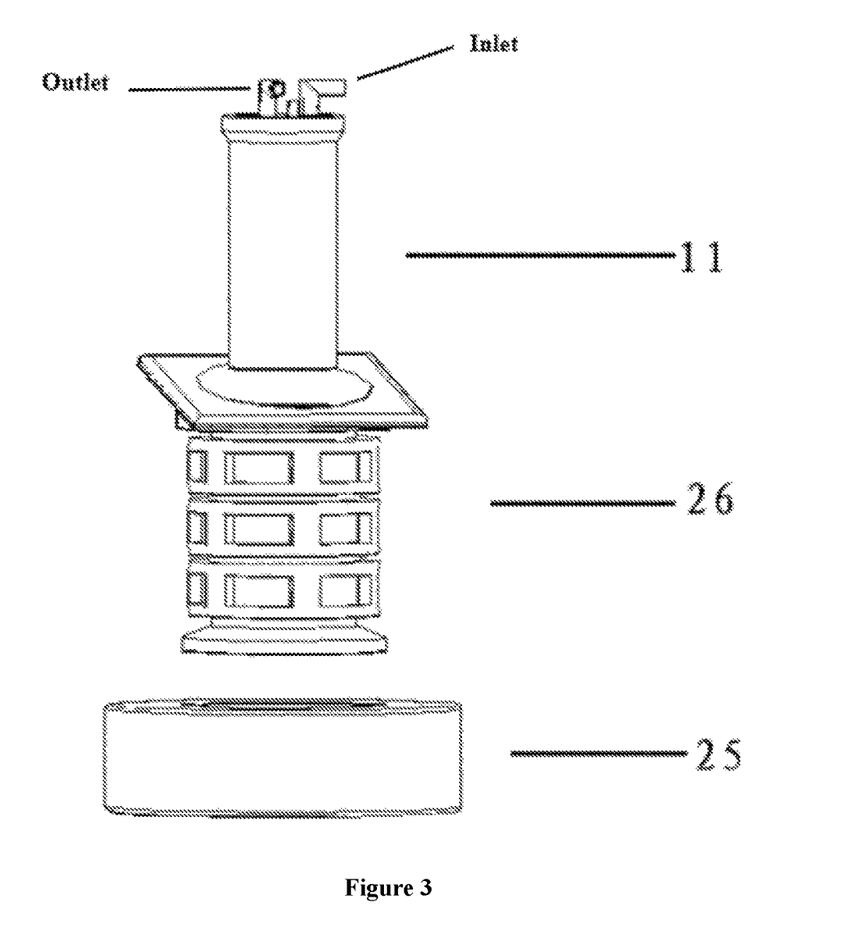
FIG. 3 is structural view 2 of the circulating hyperthermic perfusion and heating device provided by the present invention.
Figure 5:
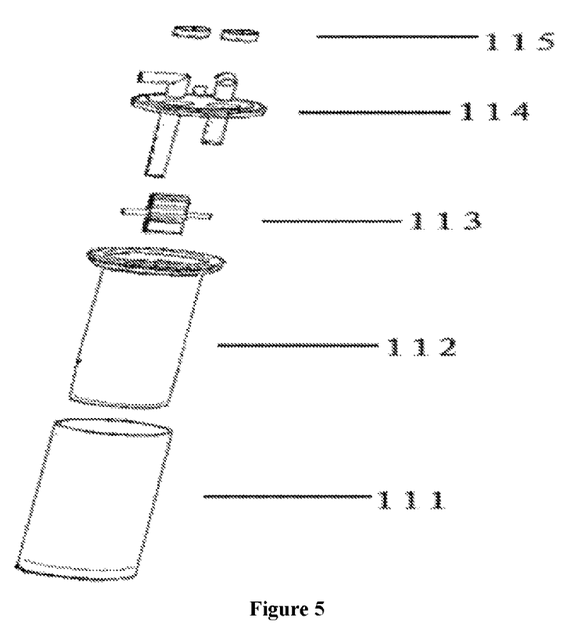
FIG. 5 is a structural view 1 of the heating tank provided by the present invention.
Figure 6:
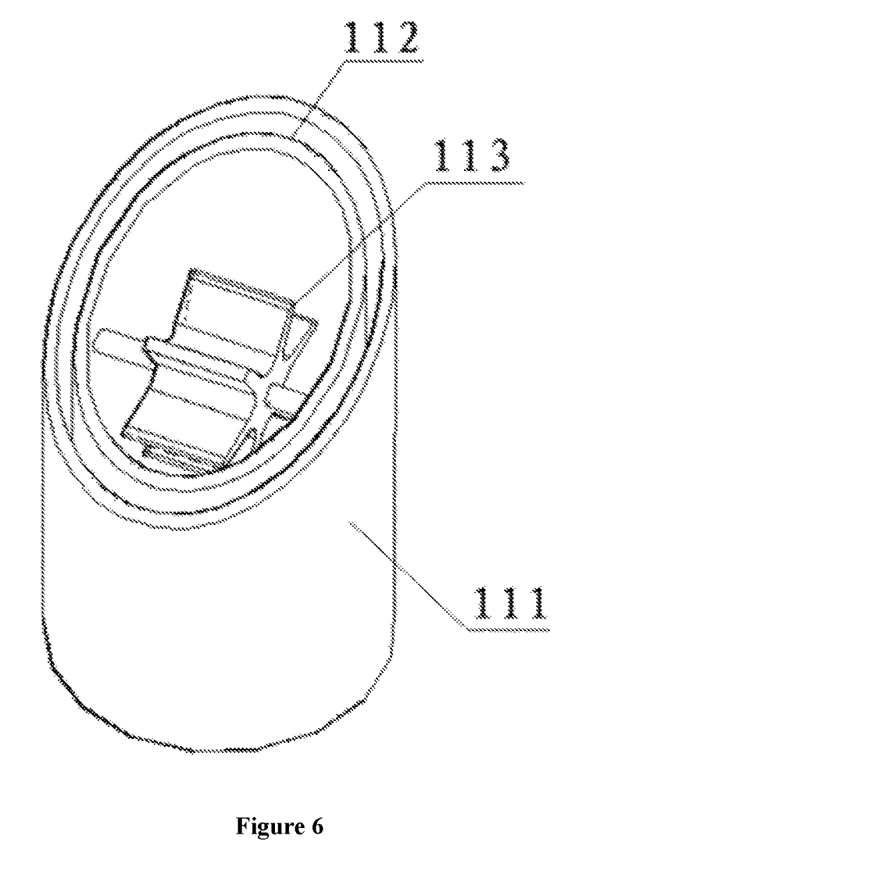
FIG. 6 is a structural view 2 of the heating tank provided by the present invention.
Figure 7:
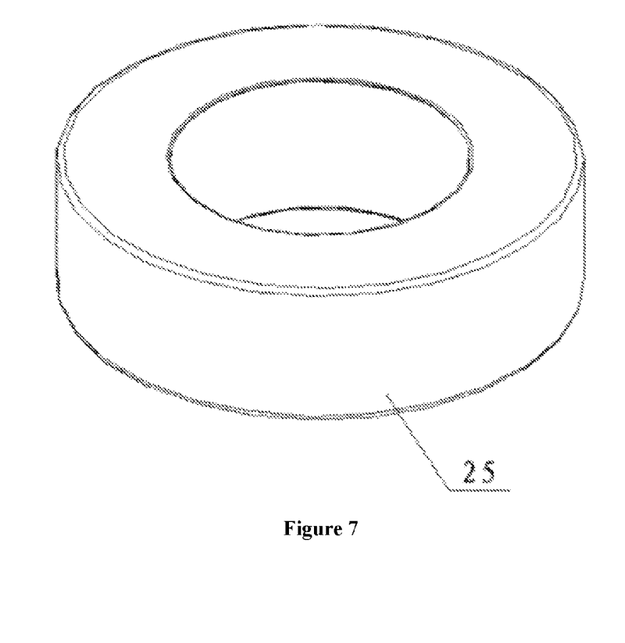
FIG. 7 is a structural view of the molecular ring provided by the present invention.

The perfusion device includes an inlet connecting member in connection with a body cavity, an outlet connecting member in connection with the body cavity, an infusion member and the dual-layer heating tank 11; the inlet connecting member is communicated with the outlet connecting member, while the inlet connecting member and the outlet connecting member are both connected with the infusion member through a tee joint; the inlet connecting member and the outlet connecting member are respectively connected with the heating tank through a connecting pipe; the body cavity, the inlet connecting member, the heating tank and the outlet connecting member are connected in turn to form a system of external circulation; an inlet and an outlet of the heating tank connected through a right row of circulating pipes to form a closed loop which is of internal circulation; the heating tank 11 includes an outer heating tank 111 and an inner heating tank 112 which are sleeved together; a closed cavity with an inlet and an outlet is formed between the inner heating tank 112 and the outer heating tank 111; the inner heating tank is internally and horizontally provided with an impeller 113; the inner heating tank is provided with an upper heating tank cover 114 with inlet and outlet pipes and a temperature control and detection sensor implanting entrance 12; the temperature control and detection sensor implanting entrance 12 is internally provided with a temperature control and detection sensor for monitoring and the liquid temperature in the heating tank and a sensor rubber plug 115; the heating tank 11 can store refluxing liquid or liquid injected by the infusion member, and the heating tank is placed in the sleeve 263 of the heater. In this embodiment, the right circulating pipe includes a connecting pipe 23, a tee joint 20, a connecting pipe 24 and a temperature buffering device 19.

Furthermore, the closed cavity formed between the inner heating tank 112 and the outer heating tank 111 is filled with radiative substances which kill cancer cells. The radiative substance can radiate harmful cancel cells and successfully achieve the radiation killing effect. The heating tank in combination with the molecular rings can radiate and kill the cancer cells, and can also decompose the cell residues to avoid generating resistance to the drugs.

The molecular rings used in the present invention constitutes closed energy ring technology. Based on the quantum physics, the vibration waves of molecular rings are stored in the liquid of the heating tank and can be steadily released at a constant level; the liquid accepts the vibration wave and transmits the vibration wave along the flow direction of the liquid, and the activity of the liquid is greatly intensified by the effect of the vibration wave. The effect is to improve the properties of the circulating liquid, improve the heat exchange efficiency, decompose the bacterial residue, and avoid the generation of drug resistance.

In use, the liquid in the heating tank is heated by using the heat generated during the mutual induction among the magnetic field generators, the induction coil wound on the sleeve and the inductor placed in the heating tank 11 in the heater; during the liquid circulation, the liquid entering the heating tank automatically flows to impact the impeller and drive the impeller to rotate, thus fulfilling the aim of stirring liquid, making the water temperature in the heating tank uniform, avoiding large differences in the temperature of the upper and lower layers due to non-uniform heating and effectively preventing the occurrence of excessive water temperature shock. Meanwhile, the molecular rings kill the cancer cells in the liquid of the heating tank and decompose the cancer cells, therefore the water temperature can be uniform and a good perfusion effect can be achieved by the effect of the impeller, heater and molecular ring.

The outlet connecting member includes an outlet connector 1, an outlet temperature sensor disposed on the outlet connecting member 1, an outlet connecting pipe 18 and an outlet pipe clamp 3 disposed on the outlet connecting pipe 18 for clamping the outlet connecting pipe; the outlet connector 1 is connected with a cavity inserting pipe of the outlet in use; the outlet connector 1 is provided with an outlet temperature sensor implanting entrance 2; the first temperature sensor (not shown in the Figure) is installed at the outlet temperature sensor implanting entrance 2 for monitoring the temperature of the effluent of the perfused liquid. One end of the outlet connecting pipe 18 is connected with the outlet connector 1, while the other end is connected with one port of a first tee joint 20; the outlet connecting pipe 18 disposed at the front end of the outlet pipe clamp 3 is connected with a molecular filter 27 for filtering the cell molecules in the liquid in the cavity during filtration and circulation and the outlet connector 1 is connected with a drain system. Wherein, the drain system includes a liquid discharge pipe 29, a body pipe clamp I 30, a flow meter 31, two peristaltic pumps 32, a body pipe clamp II 33, and a liquid body collector 34; the liquid discharge pipe 29 is connected to the outlet connector 1; the liquid discharge pipe 29 is connected to the outlet connector 1; and the liquid discharge pipe 29 is connected with a body pipe clamp I 30, a flow meter 31, two peristaltic pumps 32, the liquid body collector and the body pipe clamp II 33 in turn; the outlet connector 1 is shunted into two paths, a first path is connected with the liquid discharge pipe 29 and a second path is directly connected with the connecting pipe 18.

The inlet connecting member includes an inlet connector 4, an outlet temperature sensor disposed on the inlet connecting member 4, an inlet connecting pipe 21 and an inlet pipe clamp 7 disposed on the inlet connecting pipe 21 for clamping the inlet connecting pipe, a drainage tube 22, and a flow meter 10; the inlet connector 4 is connected with a cavity inserting pipe of the inlet in use; the inlet connector 4 is provided with an inlet temperature sensor implanting entrance 5; the first temperature sensor (not shown in the Figure) is installed at the inlet temperature sensor implanting entrance 5 for monitoring the temperature of the perfused liquid. One end of the inlet connecting pipe 21 is connected with the inlet connector 4, while the other end is connected with one outlet of a temperature buffering device 19; another outlet of the temperature buffering device 19 is connected with a port of the first tee joint 20 through a connecting pipe 24; an inlet of the temperature buffering device 19 is communicated with a heating tank 11; the temperature buffering device 19 is also formed with a temperature detection opening and an opening for sampling, the inlet connector is also connected with a drainage tube 22 with a drainage tube clamp 6; and the end of the drainage tube 22 is provided with a drainage tube transition joint 8 for being connected with a drained liquid bottle.

The temperature buffering device 19 is a temperature buffering tank; the temperature buffering tank includes an outer temperature buffering tank and an inner temperature buffering tank which are sleeved together; the inner temperature buffering tank and the outer temperature buffering tank form a vacuum there-between; the internal temperature buffering tank is internally and horizontally provided with an inner stirrer; the internal temperature buffering tank is provided with an upper temperature buffering tank cover; the upper temperature buffering tank cover is provided with two outlets, one inlet, a temperature detection opening and a sampling opening; a first outlet of the temperature buffering tank is connected with one outlet of the inlet connector, a second outlet of the temperature buffering tank is connected with a port of the first tee joint through a connecting pipe; an inlet of the temperature buffering tank is communicated with a heating tank, the temperature buffering tank is also provided with an air exhaust pipe 14 for exhausting air in the heating tank; and the air exhaust pipe 14 is provided with an air exhaust pipe clamp 13.

The perfusion device also includes a perfused power pump 15 for providing guiding power for circulation of the perfused liquid; and the maximum lift of the perfused power pump 15 is 7 m, and the maximum pressure is 0.07 MPa. The perfused power pump is disposed on the connecting pipe 23 between the heating tank 11 and the outlet connecting member for providing the guiding power for circulation of the perfused liquid; the inlet connecting pipe 21 of the inlet connecting member is provided with the guiding power for circulation of the perfused liquid; the inlet connecting pipe 21 of the inlet connecting member is provided with a drug-feeding port 9 for injecting drugs, and used for injecting chemotherapeutics into the body cavity during the infusion therapy of the hyperthermia chemotherapy the inlet connecting pipe 21 is provided with the flow meter 10 for measuring the flow of the perfused liquid; the inlet connector is also connected with a movable inlet connecting pipe; the heating tank is provided with the air exhaust pipe 14 for exhausting air in the heating tank; one end of the air exhaust pipe 14 for exhausting air in the heating tank is connected with the heating tank 11; the air exhaust pipe 14 is provided with an air exhaust pipe clamp 13; in use, the air exhaust pipe clamp is open and closed after the air is exhausted.

The infusion member is internally provided with a thermostatic chamber to keep the temperature of the liquid in the infusion member consistent with the temperature of the environment where the machine is used such that the temperature difference is not too large; the infusion member includes a bottle needle 17, an infusion pipe and an infusion pipe clamp 16; the infusion pipe at the lower end of the infusion pipe clamp 16 is provided with a physical filter 28 for filtering impurities in the initially perfused liquid. The needle body 17 is connected with a normal saline (bottle) to fill the liquid for therapy. The infusion pipe clamp 16 is used for clamping and closing the infusion pipe. Such configuration mode is an ordinary configuration mode, therefore the description is saved here.

Figure 8:
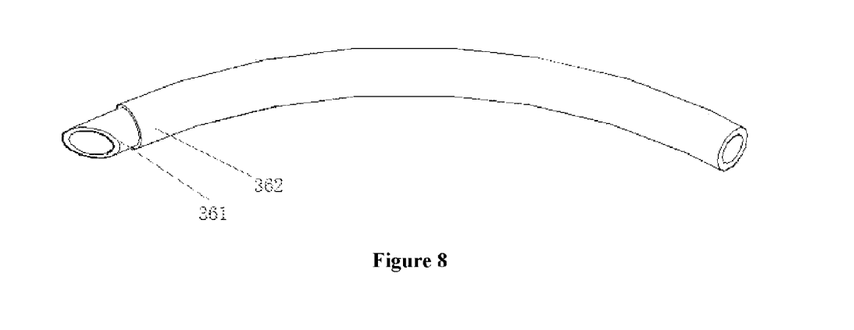
FIG. 8 is a structural view of the pipe in the inlet connecting member provided by the present invention.

Wherein, the circulating pipe in the inlet connecting member is a pipe with a dual-layer wall, and the space between the inner and outer layers of the wall is in vacuum; and due to the vacuum space, conduction and heat loss is reduced, thus realizing temperature preservation and control; the vacuum layer completely eliminates heat conduction and heat convection which occur with the existence of air and greatly reduces heat loss. Compared with the structure of the air layer, temperature loss of 5-8° can be prevented, and the heat insulation effect is good.

In use, the inlet connector 4 is inserted into the inserting pipe of the inlet cavity, and the outlet connecting pipe 1 is inserted into the inserting pipe of the outlet cavity. Using the original effusion in the body cavity, the effusion is extracted into the heating tank via the outlet connector through a perfusion power pump, and the heated effusion is injected into the body cavity through the inlet connector. This process is repeated. Or, the heating tank is injected with normal saline to form artificial effusion through the infusion member, and the artificial effusion is heated and then injected into the body cavity through the inlet connector. This process is repeated.

Through the configuration of the impeller in the heating tank, the liquid entering the heating tank automatically flows to impact the impeller and drive the impeller to rotate, thus fulfilling the aims of stirring the liquid and making the liquid temperature in the heating uniform.

Meanwhile, the present invention features multi-point heating, divided into upper, middle and lower, three layers, so heating by layer, alternative heating and concurrent heating can be employed. The heating is uniform, avoiding non-uniform temperature due to single-point or single-surface heating in the prior art.

In the heat-balance-type circulating pipe system of the present invention, the inlet connector in connection with the body cavity, the outlet connector in connection with the body cavity, and the infusion member are made from medical PVC or medical ABS materials. The maximum flow rate of the liquid in the heat-balance-type circulating pipe system is 1,200 ml/min. The volume of the heating tank 11 is 350 ml, and the total volume is 465 ml. The liquid discharge pipe 29, the inlet connecting pipe 4 and the outlet connecting pipe 28 are identical in inner diameter.

The basic principle, main characteristics and advantages of the present invention are described above. Those skilled in this field shall understand that the present invention is not limited by the above embodiments; the embodiments and the description only explain the principle of the present invention; based on the concept and scope of the present invention, various changes and improvements can be made, which shall all fall within the scope of the present invention claimed for protection. The scope of the present invention claimed for protection is defined by the Claims and the equivalent substances.

What is claimed is:

1. A heat-balance-type circulating pipe system, comprising a control system, a circulating hyperthermal perfusion heating device and a perfusion device; the circulating hyperthermal perfusion heating device and the perfusion device are both connected with the control system, and controlled by the control system; wherein the circulating hyperthermal perfusion heating device further comprises a molecular ring and a heater for heating a heating tank; the heater includes a base and a sleeve installed on the base; the sleeve is wound with an induction coil; the sleeve wound with the induction coil is coaxially sleeved with a plurality of magnetic field generators for performing induction heating on the heating tank; the plurality of magnetic field generators are externally sleeved with the molecular ring; the sleeve is provided the heating tank which is placed in the perfusion device to prevent the circulating hyperthermal perfusion heating device from generating an excessive temperature during a heating; the perfusion device includes an inlet connecting member in connection with a body cavity, an outlet connecting member in connection with the body cavity, an infusion member and the heating tank; the infusion member includes an infusion pipe clamp and a bottle needle; the inlet connecting member is communicated with the outlet connecting member, while the inlet connecting member and the outlet connecting member are both connected with the infusion member through a first tee joint; the inlet connecting member and the outlet connecting member are respectively connected with the heating tank through a first connecting pipe; the body cavity, the inlet connecting member, the heating tank and the outlet connecting member are successively connected to form an external circulation; an inlet and an outlet of the heating tank are connected through a right circulating pipe to form a closed loop which is an internal circulation; the heating tank includes an outer heating tank and an inner heating tank, the outer heating tank and the inner heating tank being sleeved together; a closed cavity is formed between the inner heating tank and the outer heating tank; the inner heating tank is internally and horizontally provided with a first inner stirrer; the inner heating tank is provided with an upper heating tank cover which is further provided with an inlet pipe, an outlet pipe and a temperature control and detection sensor implanting entrance; the temperature control and detection sensor implanting entrance is provided with a temperature control and detection sensor and a sensor rubber plug.

2. The heat-balance-type circulating pipe system according to claim 1, wherein, the outlet connecting member further comprises an outlet connector, an outlet temperature sensor disposed on the outlet connector, an outlet connecting pipe and an outlet pipe clamp disposed on the outlet connecting pipe; a first end of the outlet connecting pipe is connected with the outlet connector, while a second end of the outlet connecting pipe is connected with a first port of the first tee joint; the outlet connecting pipe at a front end of the outlet pipe clamp is further connected with a molecular filter for filtering a plurality of cells in liquid in a body cavity during filtrating and circulation; the outlet connector is connected with a drain system; the inlet connecting member includes an inlet connector, an inlet temperature sensor disposed on the inlet connector, an inlet connecting pipe, and an inlet pipe clamp disposed on the inlet connecting pipe; a first end of the inlet connecting pipe is connected with the inlet connector, while a second end of the inlet connecting pipe is connected with a first outlet of a temperature buffering device; a second outlet of the temperature buffering device is connected with a second port of the first tee joint through the first connecting pipe; an inlet of the temperature buffering device is communicated with the heating tank; the temperature buffering device is formed with a temperature detection opening and a sampling opening; the inlet connector is also connected with a drainage tube with a drainage tube clamp; and a first end of the drainage tube is provided with a drainage tube transition joint for being connected with a drained liquid bottle.

3. The heat-balance-type circulating pipe system according to claim 2, wherein, the drain system further comprises a liquid discharge pipe; the liquid discharge pipe is connected to the outlet connector; the liquid discharge pipe is successively connected with a body pipe clamp I, a flow meter, a plurality of peristaltic pumps, and a body pipe clamp II; the outlet connector is shunted into two paths, a first path is connected with the liquid discharge pipe and a second path is directly connected with the outlet connecting pipe.

4. The heat-balance-type circulating pipe system according to claim 2, the perfusion device further comprises a perfused power pump for providing a driving force for a circulation of a perfused liquid; the perfused power pump is disposed to a third connecting pipe positioned between the heating tank and the outlet connecting member; the inlet connecting pipe of the inlet connecting member is provided with a drug-feeding opening for injecting drugs and a flow meter for measuring a flow; the inlet connector is also connected with a movable inlet connecting pipe; the heating tank is also provided with an air exhaust pipe for exhausting air in the heating tank; and the air exhaust pipe is provided with an air exhaust pipe clamp.

5. The heat-balance-type circulating pipe system according to claim 2 or 4, wherein, a plurality of pipes in the inlet connecting member all have a dual-layer wall, and a space between an inner layer and an outer layer of the dual-layer wall is in vacuum.

6. The heat-balance-type circulating pipe system according to claim 1, wherein, a bottom of the base of the heater is also provided with a mixing device for uniformly mixing the liquid in the heating tank which is placed in the heater.

7. The heat-balance-type circulating pipe system according to claim 1, wherein, the closed cavity formed between the inner heating tank and the outer heating tank is filled with a plurality of radiative substances which kill cancer cells.

8. The heat-balance-type circulating pipe system according to claim 1, wherein, the infusion member is internally provided with a thermostatic chamber; a liquid outlet end of the infusion member is provided with a physical filter for filtering impurities in an initially perfused liquid.

9. The heat-balance-type circulating pipe system according to claim 2 or 4, wherein, the temperature buffering device is a temperature buffering tank; the temperature buffering tank further comprises an outer temperature buffering tank and an inner temperature buffering tank, the outer temperature buffering tank and the inner temperature buffering tank are sleeved together; the inner temperature buffering tank and the outer temperature buffering tank form a vacuum there-between; the internal temperature buffering tank is provided with an upper temperature buffering tank cover; the upper temperature buffering tank cover is provided with two outlets, one inlet, the temperature detection opening and the sampling opening; a first outlet of the temperature buffering tank is connected with one outlet of the inlet connector, a second outlet of the temperature buffering tank is connected with a port of the first tee joint through a connecting pipe; an inlet of the temperature buffering tank is communicated with a heating tank.

10. The heat-balance-type circulating pipe system according to claim 1, wherein, the magnetic field generator comprises an upper annular fixed ring and a lower annular fixed ring; a plurality of columnar magnetic bars are installed between the upper annular fixed ring and the lower annular fixed ring at an interval; and the first inner stirrer and a second inner stirrer are impellers.

* * * * *